US009562266B1

(12) United States Patent
Cameron et al.

(10) Patent No.: US 9,562,266 B1
(45) Date of Patent: Feb. 7, 2017

(54) AMINE-TERMINATED APTAMER FUNCTIONALIZED SURFACE PLASMON RESONANACE SENSORS, METHODS OF MAKING AND METHODS OF USING SAME

(71) Applicant: The University of Toledo, Toledo, OH (US)

(72) Inventors: Brent D. Cameron, Waterville, OH (US); Dong-Shik Kim, Sylvania, OH (US); Rui Zheng, Toledo, OH (US); Byung-Wook Park, Toledo, OH (US)

(73) Assignee: The University of Toledo, Toledo, OH (US)

( * ) Notice: Subject to any disclaimer, the term of this patent is extended or adjusted under 35 U.S.C. 154(b) by 997 days.

(21) Appl. No.: 13/740,334

(22) Filed: Jan. 14, 2013

Related U.S. Application Data

(60) Provisional application No. 61/586,760, filed on Jan. 14, 2012.

(51) Int. Cl.
*G01N 33/551* (2006.01)
*C12Q 1/68* (2006.01)

(52) U.S. Cl.
CPC .......... *C12Q 1/6876* (2013.01); *G01N 33/551* (2013.01)

(58) Field of Classification Search
None
See application file for complete search history.

(56) References Cited

U.S. PATENT DOCUMENTS

| 4,444,879 | A | * | 4/1984 | Foster | .................. | G01N 33/545 422/400 |
|---|---|---|---|---|---|---|
| 7,317,533 | B2 | | 1/2008 | Chiarello et al. | | |
| 7,847,948 | B2 | | 12/2010 | Lee | | |
| 7,871,789 | B2 | | 1/2011 | Yonehara et al. | | |
| 7,951,529 | B2 | | 5/2011 | Li et al. | | |
| 8,023,109 | B2 | | 9/2011 | Yamamichi et al. | | |
| 8,026,071 | B2 | | 9/2011 | Chin et al. | | |
| 2005/0014135 | A1 | | 1/2005 | Hill et al. | | |
| 2006/0134695 | A1 | | 6/2006 | Quinn | | |
| 2007/0148670 | A1 | | 6/2007 | O'Malley | | |
| 2009/0239766 | A1 | | 9/2009 | Chen et al. | | |
| 2009/0263787 | A1 | | 10/2009 | Chen et al. | | |
| 2009/0275061 | A1 | | 11/2009 | Chen et al. | | |
| 2009/0280575 | A1 | | 11/2009 | Chen et al. | | |
| 2009/0311699 | A1 | | 12/2009 | Chen et al. | | |
| 2009/0325190 | A1 | | 12/2009 | Chen et al. | | |
| 2010/0004872 | A1 | | 1/2010 | Chen et al. | | |
| 2010/0009464 | A1 | | 1/2010 | Chen et al. | | |
| 2010/0021882 | A1 | | 1/2010 | Chen et al. | | |
| 2010/0021930 | A1 | | 1/2010 | Chen et al. | | |
| 2010/0028856 | A1 | | 2/2010 | Chen et al. | | |
| 2010/0047815 | A1 | | 2/2010 | Chen et al. | | |

(Continued)

OTHER PUBLICATIONS

Meng et al., "Development of a highly specific amine-terminated aptamer functionalized surface plasmon resonance biosensor for blood protein detection", Biomedical Optics Express, 2011, vol. 2, No. 9, pp. 2731-2740.

*Primary Examiner* — Chris L Chin
(74) *Attorney, Agent, or Firm* — MacMillan, Sobanski & Todd, LLC

(57) ABSTRACT

Sensors for target entities having functionalized thereon, at least one amine-terminated aptamer specific to the target entity, and methods of making and using the same are described.

20 Claims, 3 Drawing Sheets

(56) References Cited

U.S. PATENT DOCUMENTS

| | | |
|---|---|---|
| 2010/0053610 A1 | 3/2010 | Lee |
| 2010/0068697 A1* | 3/2010 | Shih .................... G01N 29/022 |
| | | 435/5 |
| 2010/0086920 A1 | 4/2010 | Chen et al. |
| 2010/0105053 A1 | 4/2010 | Cho et al. |
| 2010/0112722 A1 | 5/2010 | Mrksich et al. |
| 2010/0279422 A1 | 11/2010 | Chen et al. |
| 2010/0317128 A1* | 12/2010 | Harada ................ C12Q 1/6816 |
| | | 436/501 |
| 2011/0236991 A1 | 9/2011 | Lu et al. |
| 2011/0287557 A1 | 11/2011 | Zhang et al. |

\* cited by examiner

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' NH2-(CH2)6

<400> SEQUENCE: 1
ggttggtgtg gttgg                                                         15

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' NH2-(CH2)6

<400> SEQUENCE: 2
ctatcagtcc gtggtagggc aggttggggt gact                                    34
```

AMINE-TERMINATED APTAMER FUNCTIONALIZED SURFACE PLASMON RESONANACE SENSORS, METHODS OF MAKING AND METHODS OF USING SAME

CROSS-REFERENCE TO RELATED APPLICATIONS

This application claims the benefit of U.S. Provisional Application Ser. No. 61/586,760 filed Jan. 14, 2012, the entire disclosure of which is expressly incorporated herein by reference.

STATEMENT REGARDING FEDERALLY SPONSORED RESEARCH

The invention was made with not made with any government support and the government has no rights in the invention.

SEQUENCE LISTING

The instant application contains a Sequence Listing which has been submitted via EFS-web and is hereby incorporated by reference in its entirety. The ASCII copy, created on Jan. 8, 2013, is named 420_53326_SEQ_LIST_D2012_07 txt, and is 883 bytes in size.

TECHNICAL FIELD AND INDUSTRIAL APPLICABILITY OF THE INVENTION

The present invention relates to amine-terminated aptamer functionalized surface plasmon resonance (SPR) sensors, methods of making and methods of using the same.

BACKGROUND OF THE INVENTION

Detecting specific molecules is a crucial task for medicine, biotechnology, chemical and biodefense, and environmental protection. Many new detection systems are developed every year with increasing specificity and sensitivity. These systems include the latest developments in biotechnology and nanotechnology. All of them have one common feature: they employ sophisticated and expensive equipment for the processing and/or the readout of the results.

The direct detection of blood proteins can benefit a number of scientific and clinical applications, such as in monitoring the ratio of specific protein glycation in diabetes, biomarkers for drug research and environmental monitoring, cancer diagnostics and treatment, and the like. The current clinical and laboratory measurement techniques for blood proteins are boronate affinity immunoassay, high-performance liquid chromatography (HPLC) and capillary based systems, which are time consuming and costly.

More efficient and fast response measurement methods could greatly benefit and enhance related application areas, especially for developing the next generation of portable handheld diagnostic devices capable of real-time analysis. Several optics-based diagnostic techniques, such as near-infrared spectroscopy, polarimetry, optical coherence tomography, surface plasmon resonance (SPR), Raman and fluorescence spectroscopy have recently been investigated for monitoring blood components.

SUMMARY OF THE INVENTION

In a first broad aspect, there is provided herein a sensor for detecting the presence of a target entity, comprising an aptamer probe having an amine-terminated end that is capable of being linked to a substrate. The sensor is capable of interacting with the target entity. When the sensor is excited by an energy source either in the absence of specific interaction between the target entity and the aptamer probe, a baseline signal is emitted. When the sensor is excited by an energy source in the presence of specific interaction between the target entity and the aptamer probe, a detection signal is emitted. The baseline signal is different from the detection signal such that any presence of the target entity is detected.

In certain embodiments, the aptamer probe includes a nucleotide sequence which specifically interacts with the target entity.

In certain embodiments, the target entity is one or more of: a large biomolecule, a small biomolecule, an organic molecule, a small molecule, a nucleic acid, a metal ion, a protein, an enzyme, a peptide, a drug, a dye, a cancer cell, a virus, a hormone, or a microorganism. In certain embodiments, the protein is a blood protein.

In certain embodiments, the aptamer probe comprises an aptamer and an attached amine moiety.

In certain embodiments, the aptamer probe includes a self-assembled monolayer (SAM) linker between the substrate and the amine moiety.

In certain embodiments, an amine-terminated aptamer probe can be linked to a substrate by 3-mercaptopropionic acid (MPA).

In certain embodiments, the sensor has a tunable detectable range capable of pM to nM detection, based on the linker characteristics.

In another broad aspect, there is provided herein a method of determining the presence of a target entity in a sample comprising: i) contacting the sample with a sensor as described herein; ii) exciting the sensor with an energy source; and, iii) determining the strength of a signal emitted by the sensor, thereby determining whether the target entity is present in the sample.

In certain embodiments, the energy source is measured using surface plasmon resonance (SPR).

In certain embodiments, the method has a response time of less than 1 minute. In certain embodiments, the method has a response time of less than 1 minute at about room temperature.

In another broad aspect, there is provided herein a kit for the detection of a target entity, comprising: a sensor as described herein; and at least one container containing the sensor, where a sample may be added to the container.

In another broad aspect, there is provided herein a method for making a sensor, comprising: i) immobilizing a self-assembled monolayer (SAM) linker to a substrate; and ii) immobilizing an amine-terminated aptamer to the SAM linker.

In another broad aspect, there is provided herein a method for making a sensor of, comprising: i) functionalizing a substrate with a self-assembled monolayer (SAM) linker; ii) exposing the functionalized substrate of step i) to a composition having an amine moiety sufficient for the amine moiety to be immobilized on the SAM linker; iii) exposing the amine-functionalized substrate of step ii) to at least one aptamer sufficient for the aptamer to be immobilized on the amine moiety; and iv) exposing the amine-terminated aptamer functionalized substrate of step iii) or iv) to a blocking agent sufficient to block non-occupied SAM sites activated by the amine moiety. In certain embodiments, the method can include removing any non-specifically immobilized aptamer.

In certain embodiments, the composition having the amine moiety is one or more of: N-hydroxysuccinimide (NHS) and N-(3-dimethylamnopropyl)-N-ethylcarbodiimide hydrochloride (EDC).

In another broad aspect, there is provided herein a method for detecting blood proteins using a sensor as described herein.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

Figure 1:
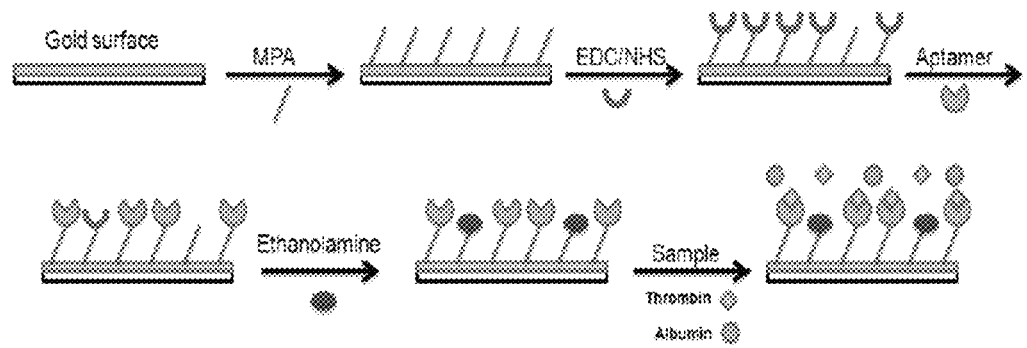
FIG. 1 Schematic diagram of a sensing surface functionalization method.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The term "aptamers" as used here indicates oligonucleic acid or peptide molecules that are capable to bind a specific target entity. In general, aptamers are artificial oligonucleotides which can serve as antibody mimics because of their high affinity and selectivity for various target compounds ranging from small molecules, such as drugs and dyes, to complex biological molecules such as enzymes, peptides, and proteins. Custom aptamers can be identified from random oligonucleotide libraries for specific target compounds by an in vitro iterative process called Systematic Evolution of Ligands by Exponential Amplification (SELEX). Aptamers can form a 3D structure serving as receptors specific to their target compounds similar to antibodies. Aptamers also have a number of advantages over antibodies such as a tolerance to wide ranges of pH and salt concentrations, heat stability, ease of synthesis, and cost efficiency. The specificity and affinity of aptamers are comparable, if not higher, to antibodies. Aptamers are also capable of being reversibly denatured for the release of target compounds, which makes them perfect receptors for biosensing applications.

For example, aptamers can be comprised of single-stranded (ss) oligonucleotides and/or be chemically synthesized peptides that have been engineered through repeated rounds of in vitro selection, or equivalent techniques identifiable by a skilled person, to bind to various targets.

Also, the aptamers can be single-stranded oligonucleotides with a length of tens of nucleotides, where the aptamers exhibit high affinity and specificity towards any given target molecule. The aptamers can have highly defined tertiary structures which allow such aptamers to form stable and specific complexes with a range of different targets. Non-limiting examples of target range from small molecules (such as amino acids) to highly complex molecules (such as proteins and whole viruses).

The term "sensor" as used herein indicates a device that measures a physical quantity and converts it into a signal which can be read by an observer or by an instrument. As is understood, a sensor is calibrated against known standards. Accordingly, a sensor can be used to capture a target entity by exploiting the affinity of aptamer to the target entity, and can be detected using techniques identifiable by a skilled person upon reading of the present disclosure.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: spectra or images from a target of interest or a probe attached to the target.

The terms "target," "target entity" as used herein indicates an analyte of interest. The term "analyte" refers to a substance, compound or component whose presence or absence in a sample has to be detected. Analytes include but are not limited to biomolecules and in particular biomarkers. The term "biomolecule" as used herein indicates a substance compound or component associated to a biological environment including but not limited to sugars, amino acids, peptides proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state.

In several embodiments, distribution of metal on a suitable substrate results in a metal coated surface of a suitable substrate. The term "substrate" as used herein indicates an underlying support or substratum. Exemplary substrates include solid substrates, such as glass plates, microtiter well plates, magnetic beads, silicon wafers, silica nanosphere and additional substrates or surfaces identifiable by a skilled person upon reading of the present disclosure.

Surface plasmon resonance (SPR) is a member of a family of spectroscopic techniques based on evanescent wave optics. It is used for determination of refractive index, dielectric constant, and layer thickness with high sensitivity. By itself, however, SPR is not a selective sensing technique and requires adaptation for specific target identification and quantification.

While the use of a self-assembled monolayer (SAM) as a linker and coadsorbent thiol-modified aptamers together to form an aptamer-SAM matrix on a gold surface has been attempted, there has not been acceptance of such, in part since cost of the thiol-modified aptamers is much higher than the non-modified or amine-modified aptamers. Also, the uniformity and density of the SAM are also not guaranteed from sample to sample.

Described herein is a 3-mercaptopropionic acid (MPA) SAM based coupling system that now provides a stable and repeatable modification of the sensor surface. Electrochemical Impedance Spectroscopy (EIS) was utilized to monitor the formation of the SAMs on the gold surfaces. Aptamer binding capacity was then determined by a magnetic beads (MBs) coupling method. The developed sensor has an optimal detectable range of 5-1000 nM with good reversibility, sensitivity and selectivity. Furthermore, the sensor can be used for the direct detection of other blood proteins for clinical applications. A schematic diagram of a sensing surface functionalization method is shown in FIG. 1.

In a particular aspect, there is described herein the use of a two-step immobilization method, in which a SAM is first immobilized on a substrate, followed by immobilization of one or more types of aptamer monomers on the substrate. This embodiment provides a more cost effective and controllable method compared to adding all of the modifications to the aptamer monomer at once.

In another particular aspect, the method includes specifically designing the SAM, e.g., optimizing the hydrocarbon length and introducing co-adsorbents, while still using the simple amine-modified aptamer as the receptor to improve the sensitivity and selectivity.

Since the surface density of immobilized aptamer affects the efficiency of target capture, and the surface coverage can be modified by the aptamer immobilization concentrations, in certain embodiments, relatively high aptamer concentrations (e.g., 5 μM) can be used to guarantee the density and the uniformity of the surface. Further, in certain embodiments the presently described method can include optimizing the aptamer immobilization concentrations to improve the performance of the sensor.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

The value of the present invention can thus be seen by reference to the Examples herein.

Example 1

Materials

The identified aptamers were synthesized by Integrated DNA Technologies (Coralville, Iowa), including a 15 bp aptamer (APT1): 5'-NH$_2$—(CH$_2$)$_6$-GGTTGGTGTGGT-TGG-3' [SEQ ID NO:1], and a 34 bp aptamer (APT2): 5'-NH$_2$—(CH$_2$)$_6$-CTATCAGTCCGTGGTAGGGCAGGT-TGGGGTGACT-3'. [SEQ ID NO:2].

Tosylactivated MBs were purchased from Invitrogen (Carlsbad, Calif.). All other chemicals were purchased from Sigma Aldrich (Carlsbad, Calif.) at the highest purity available. Aptamer solutions were prepared with 1M pH 8 phosphate buffer. The 3-mercaptopropionic acid (MPA) solution was prepared in ethanol. Protein sample solutions were prepared using a 0.1M pH 7.2 PBS buffer solution with 5 mM KCl and 1 mM MgCl$_2$. The phosphoric acid (PPA) used was 100 mM. All other solutions were prepared in deionized (DI) water.

Instrumentation

SPR measurements were performed using a commercial grade SensiQ Discovery system (ICx Technologies, Arlington, Va.) at 25° C. This sensor is based on a Kretschmann configuration, in which the light from a light-emitting diode (LED) integrated with a prism is firstly polarized and then internally reflected from a gold surface. The angle of light reflection and the relative intensity was measured with a photodiode array. When the sample solution is applied to the sensing surface, the SPR profile minimum (also known as the SPR angle) will shift as a function of the refractive index of the loaded sample, giving a real time refractive index reading (although, by itself the sensor is not specific/selective for any given target). The SPR response profile was recorded by the SensiQ software and then processed within MATLAB®.

Measurements

Electrochemical impedance spectroscopy (EIS) measurements were carried out using a Gamry Reference 600 potentiostat (Warminster, Pa.) in 5 mM Fe(CN)$_6^{3-}$/Fe(CN)$_6^{4-}$ solution with KCl as a supporting electrolyte. All the experiments were carried out at room temperature with the solutions purged with nitrogen gas for 15 minutes and the nitrogen blanket was maintained during the experiments. The experiments were performed at 25° C. Impedance spectra were collected in the frequency range from 0.1 Hz to 100 kHz with a potential amplitude of 5 mVrms at 10 points per decade. EIS results were analyzed by fitting the experimental impedance data to electrical equivalent circuit models. Parameters of the electrical-equivalent circuits were obtained by fitting the impedance function to the measured Bode and Nyquist plots with a complex nonlinear least square (CNLS) program built into the Gamry EIS 300 electrochemical impedance spectroscope.

Aptamer coupling to the MBs was performed as followed: 10 nmol of amine modified aptamer was coupled to 10 mg washed MBs in a shaker incubator at 37° C. for 18 hours. The unoccupied binding sites were blocked by Bovine Serum Albumin (BSA). The MBs were washed thoroughly and then 10 nmol of thrombin was mixed with the aptamer-coupled MBs for 2 hours in a shaker at room temperature. The control group was prepared by exactly the same method except for the absence of aptamers. The total and unbounded proteins were measured with a carboxyl functionalized SPR sensor provided by SensiQ.

To use an aptamer-based SPR sensor for detecting blood proteins, thrombin and anti-thrombin aptamer were chosen for demonstration purposes. Gold slides were prepared by physical vapor deposition (PVD) forming a 1 nm layer of titanium and a 50 nm layer of gold onto pre-cleaned microscope cover slides. These were then washed by copious amounts of DI water and ethanol. They were dried in nitrogen gas before usage.

To functionalize the gold slides, they were immersed in the 10 mM MPA solution for 30 min and then washed with ethanol and DI water. After the slides were dried, then they were immersed in a solution of N-hydroxysuccinimide (NHS) and N-(3-dimethylamnopropyl)-N-ethylcarbodiimide hydrochloride (EDC) (NHS 0.2M, EDC 0.05M) for 30 min. The slides were then washed with DI water and then immersed in the 5 µM aptamer solution. Finally, the slides were rinsed with the PBS buffer to flush off non-specifically adsorbed proteins. Then the slides were ready for measurement. This two-step surface functionalization process is schematically illustrated in FIG. 1.

Non-coated (i.e., no gold) SensiQ base sensors were custom modified with the developed gold based SPR sensing surfaces. Specifically, freshly prepared aptamer-immobilized gold substrates were coupled to the stripped sensors with index matching optical oil. This was followed by then loading of 100 µL 1 M ethanolamine (EA) at a flow rate of 20 µL/min to block the non-occupied MPA sites activated by the EDC/NHS, followed by an injection of 100 µL of 100 mM phosphoric acid (PPA) at 50 µL/min to remove the non-specific binding. The running buffer was 0.1 M pH 7.2 PBS. The sensor was first normalized with the buffer for 10 min, then the thrombin sample (25 µL) at concentrations of 5 nM, 25 nM, 50 nM, 250 nM 500 nM, 1000 nM, 2000 nM were loaded at 5 µL/min. Samples with BSA were all prepared with 400 nM BSA. All data was recorded at 290 s, 300 s, and 310 s after the sample injection and averaged. Sensor regeneration was performed by the injection of 100 µL PPA at 50 µL/min followed by washing with the running buffer.

Results

EIS Measurement

Figure 2:
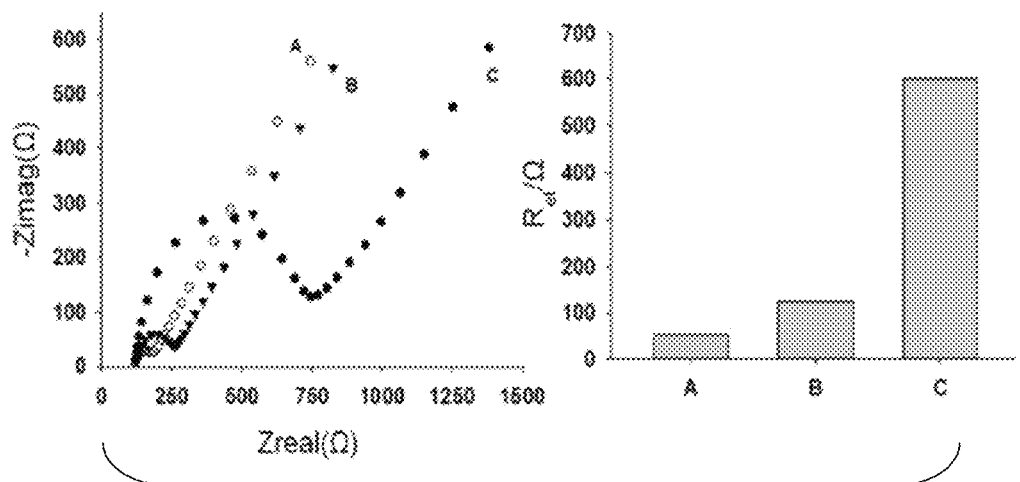
FIG. 2. Nyquist plots of impedance spectra obtained in 100 mM PB solution (pH 7.2) containing 5 mM $Fe(CN)_6^{3-}$/$Fe(CN)_6^{4-}$ (Column A) Bare Au; (Column B) Au/MPA/EDC-NHS/EA/PPA; (Column C) Au/MPA/EDC-NHS/EA/PPA/APT1. The right plot shows the ($R_{et}$) of each layers. Impedance spectra were collected in the frequency range from 0.1 Hz to 100 kHz with a potential amplitude of 5 mV rms at 10 points per decade.

The successful immobilization of each functionalized layer was confirmed through EIS measurements. FIG. 2 shows the Nyquist plots of impedance spectra at different electrodes. The bare gold electrode represented a very small circle at high frequencies, suggesting a very low electron transfer resistance to the redox probe dissolved in the electrolyte solution (curve A). When the MPA was immobilized on the electrode and treated with EA and PPA, the electron transfer resistance ($R_{et}$) increased to 125Ω, (curve B). Then, when 5 µM of the APT1 aptamer was added and bound with the SAM, $R_{et}$ increased to 600Ω (curve C). Note that the reactive sites on the gold electrode were blocked by EA (ethanolamine) to prevent non-specific adsorption of aptamers onto the gold surface, thus making sure that the aptamers were attached only to the SAM. The $R_{et}$ increase is attributed to the electrostatic repulsion between the immobilized aptamer and the redox probe, causing a barrier for the interfacial electron transfer. These results show successful immobilization of the SAM layer onto the gold surface and stable bonding of the aptamer to the SAM MB Based Maximum Binding Capacity After the modified MBs were thoroughly washed, thrombin was added and the concentration change was measured using a carboxyl modified SPR sensor. The refractive index is controlled only by the concentration change of the added thrombin. Other experimental variables such as protein degeneration and temperature had minor influences on SPR results and thus were not considered.

Figure 3:
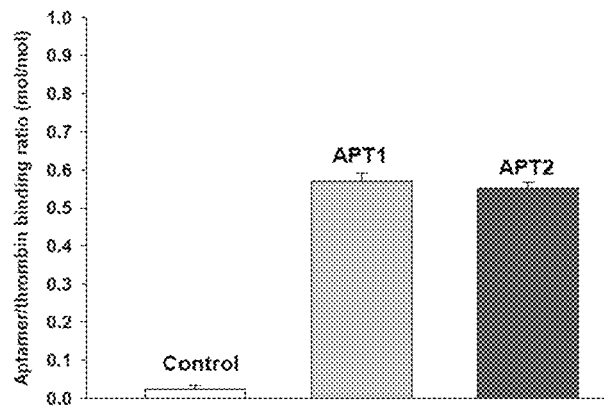
FIG. 3. Graph showing aptamer/thrombin binding ratio in mol by the MBs coupling method.

As shown in FIG. 3, the concentration change of thrombin was insignificant for the control group (less than 3%) which was not functionalized by the aptamer. This shows that the concentration change in the two experimental groups was mainly due to the binding between the aptamer and thrombin. For the APT1 and APT2 groups, the mixture of aptamer functionalized MBs and thrombin solution was allowed to react for 18 hours and the reaction was considered to be completed based on the MB manufacturer's specifications. Thus, the final concentration reflected the maximum mol/mol binding capacity of aptamer to thrombin.

The results showed the binding ratio of APT1 (57.1%) has a slightly better capacity than APT2 (55.2%). Both aptamers had more than 50% mol/mol binding ratio to thrombin, indicating that they are good receptor candidates for thrombin sensing applications. It is to be understood that, in certain embodiments, not all the aptamers may bind to the MBs and therefore the actual binding capacity of the binding aptamers toward target compound/s may be slightly greater. In this example, the MBs were used to determine the maximum binding capacity of the aptamers.

The Control group consists of MBs without aptamer functionalization and all binding sites blocked by BSA. The APT1 and APT2 groups consist of MBs functionalized by the respective aptamers with the unoccupied binding sites blocked by BSA. The error bars represent the standard deviation of the values determined from three samples.

SPR Results

Figure 4:
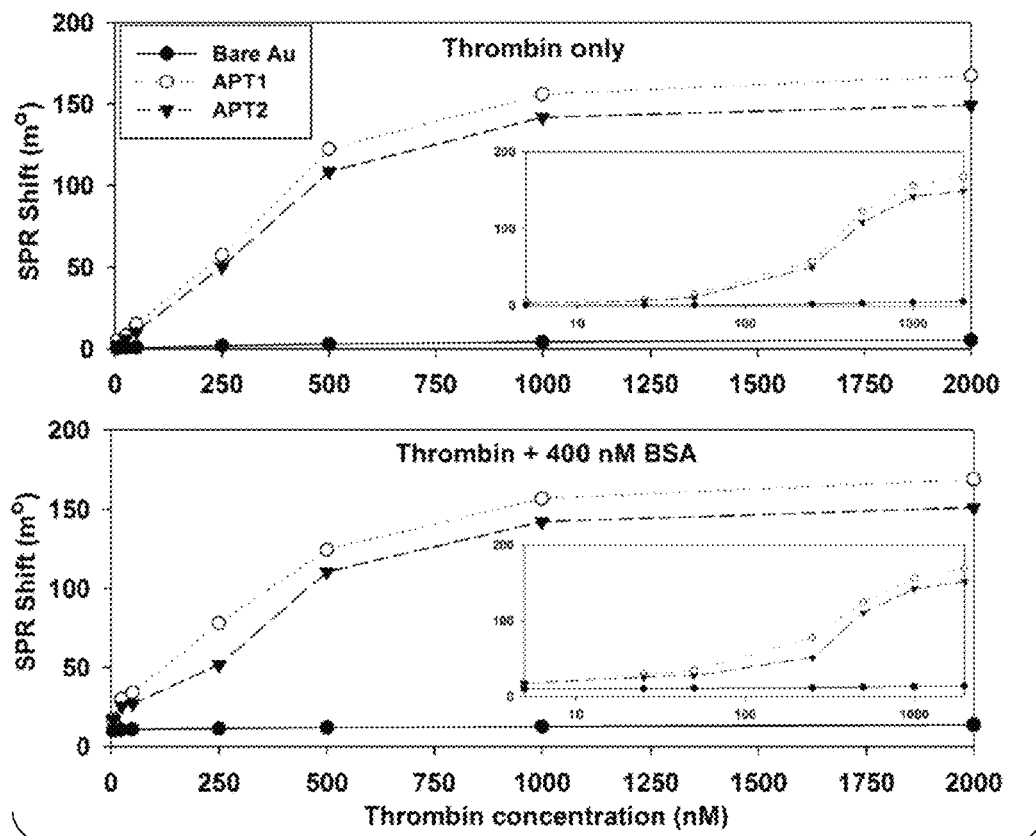
FIG. 4. Graphs showing SPR response of bare Au and aptamer-modified sensors. All data points were averaged from 3 experimental data readings. Samples were thrombin only (top plot) and thrombin with 400 nM BSA (bottom plot). The inlay plots are same data plotted on logarithmic scale to allow for better visualization at lower concentrations.

Two different aptamers were immobilized on gold surfaces and the binding performance of each one was compared. For reference, samples of different thrombin concentrations (5 nM, 25 nM, 50 nM, 250 nM, 1000 nM, 2000 nM) were individually loaded onto a bare Au, an APT1, and APT2 sensor, respectively. A secondary experiment was then performed using the same thrombin concentrations, however, with a 400 nM BSA confounding component added to each thrombin sample for comparison. As shown for the "Thrombin only" experiment in FIG. 4, the SPR shifts were very low for the bare Au sensor surface even for the relatively high thrombin concentrations.

In contrast, for the aptamer modified sensors the SPR shifts were significantly enhanced and the optimal detection range was 5 nM to 1000 nM (linear range). As shown in the "Thrombin+400 nM BSA" experiment in FIG. 4, the prior experiment was replicated, however, with a large 400 nM BSA confounding concentration component added to each thrombin sample concentration. As compared to the thrombin only group, the responses are nearly identical indicating the developed APT1 and APT2 sensors are highly specific to only thrombin.

Figure 5:
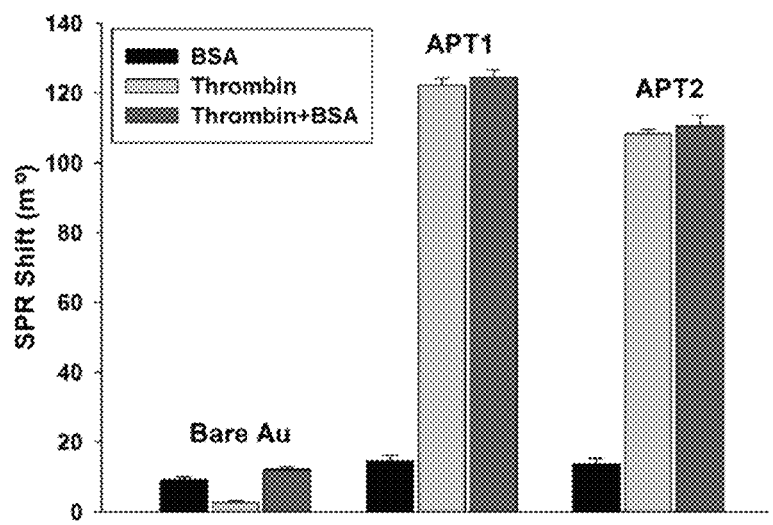
FIG. 5. Graph showing SPR responses of different sensing surfaces for 400 nM BSA (BSA group), 500 nM thrombin (Thrombin group), and 500 nM thrombin with 400 nM BSA (Thrombin+BSA group). The error bars represent the standard deviation of the values determined from three freshly prepared samples.

This is further illustrated in FIG. 5, which shows the SPR shift for the 500 nM thrombin concentration with and without 400 nM of BSA. Adding BSA to the sample had minimal effect on the SPR response for the aptamer modified sensors, indicating a good selectivity of the sensor toward thrombin. This is in contrast to the bare Au sensor, which experienced a significant change between the thrombin samples with and without BSA. The APT1 modified sensor did have a slightly higher shift than the APT2 sensor for all the thrombin concentrations. The slope of the fitting line for APT1 is also slightly larger than APT2 in the linear response range (FIG. 6), again demonstrating a better sensitivity. These two aptamers bind to different sites of thrombin, thus the affinity to the target is different in both the interfacial binding environment and in solution.

In the MBs binding tests, the APT1 had a slightly higher binding capacity than APT2, which corresponds to the SPR results in terms of sensitivity of the functionalized sensor. This may be due to the smaller aptamer having a greater probability to access the binding sites of the target protein. Also, larger aptamers have more complicated secondary structures that require an extra spatial flexibility to form bonding with target compounds.

As Example 1 shows, the MPA layer has excellent coverage rate on gold and is useful for antibody immunization for biosensing purposes. MPA is cost effective and the related SAMs are straightforward to prepare. These results also show that the amine-modified aptamer can be readily immobilized onto the MPA layer and the sensor performance was comparable to antibody-based sensors.

Three sensing slides were prepared for each aptamer and also the control group. The sensor to sensor performance was consistent when using the freshly prepared samples, yielding relatively small errors for each measurement and averaging less than 2% standard deviation of the total signal (error bar showed in FIG. 5).

Adding BSA did introduce a slightly larger error and by lowering the flow rate and increasing the sample loading time, the error can be reduced although deemed not significant enough to be considered. The majority of the error is thought to be caused by temperature variance; as such, in some embodiments, placing the sensor in a temperature controlled environment can help increase the accuracy.

The sensing surface described herein had an optimal dynamic range from 5 nM to 1000 nM, which is comparable to or greater than the largest reported dynamic ranges for thrombin aptamer-based sensing techniques. Since the thrombin concentration range in the human blood is reported to be within the low nanomolar to low micromolar range, the presently described method is well suited for in vivo thrombin quantitative detection.

Figure 6:
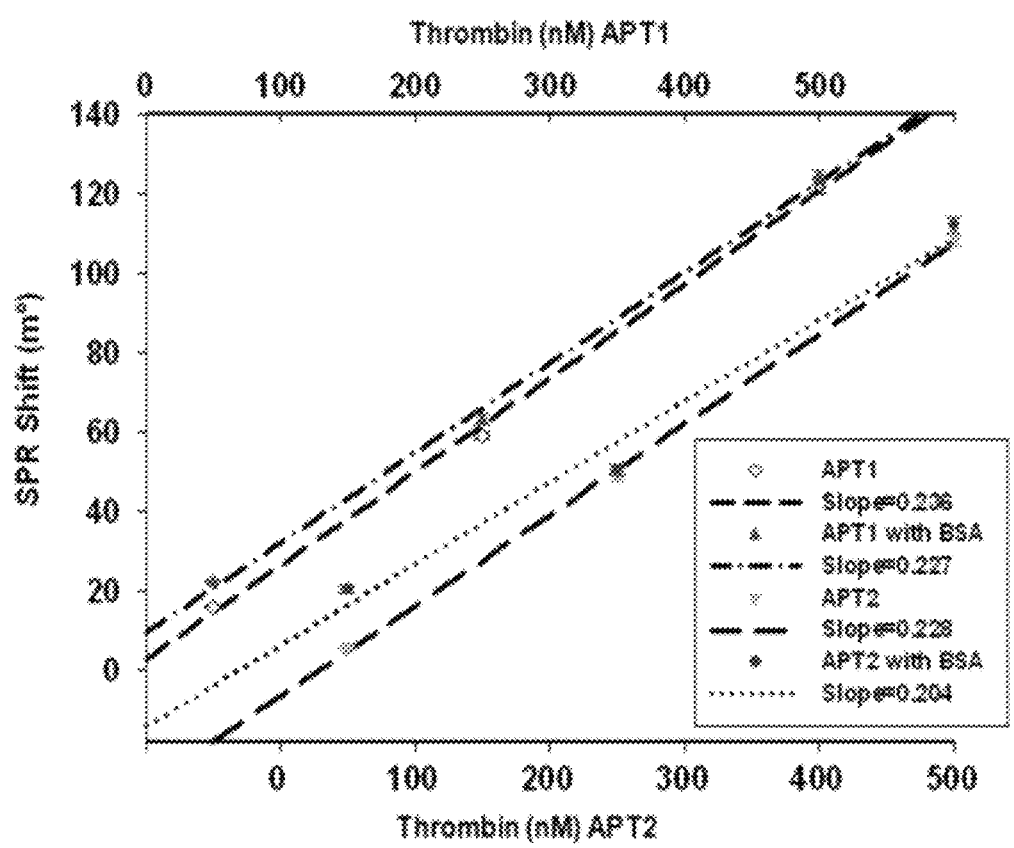
FIG. 6. Graph showing SPR responses of different sensing surfaces for 50 nM, 250 nM, 500 nM thrombin with and without 400 nM BSA, upper axis (APT1), lower axis (APT2); The zero position of lower axis has been shifted intentionally to better distinguish between data points that would be overlapping.

To test the reversibility of the sensor, fixed sample concentrations were repeatedly loaded to the sensor 10 times. The sensor regeneration was done by PPA. The average SPR response with error bars for standard deviation using thrombin concentrations of 50 nM, 250 nM and 500 nM are shown in FIG. 6. All data were obtained from freshly prepared sensing slides. The SPR response generally decreased about 0.5% for each loading for a same sample concentration. All the sensing slides maintained more than 95% of the original SPR shift response after the 10th loading. It was also noticed that the second sample loading usually had the greatest response change as compared to the following loadings. With a longer PPA injection time, the sensor recovery rate can be increased, depending on the experimental requirements. The appearance of BSA did lower the sensitivity of the sensor (e.g., in FIG. 6, the appearance of BSA did reduce the slope slightly in the response curve), although it did not affect the reversibility of the sensor. FIG. 6 also demonstrates that sensor maintained a linear response with and without the appearance of BSA in the 50 nM to 500 nM sample range.

Example 2

Other Embodiments of Sensors

In another embodiment, the sensor can include a mixed length spacer layer. In one non-limiting example, the mixed length layer can be as 11-mercaptoundecanoic acid (MUA) combined with MPA, which can be used in certain embodiments to increase the sensitivity and specificity.

In other embodiments, a mixed length spacer can be included to help form and maintain the specific shape of the immobilized aptamers.

In another embodiment, a hydrophilic group such as ethylene oxide can be inserted onto the $5^c$-end of the aptamer in order to reduce nonspecific protein binding.

In certain embodiments of the two step immobilization method described herein, spacing the aptamers can also done by adjusting the MPA SAM density, or by co-incubating ethanolamine and the aptamer at various molar ratios.

Detection of Blood Proteins

For the detection of different blood proteins, in order to find the aptamer that specifically and directly binds to the target protein of interest, a SELEX procedure can be used. Then, the developed aptamer can then be amine-terminated and immobilized onto the gold surface using one of the presently described methods in order to form a target specific sensor for almost any protein. As such, aptamers can be generated through SELEX to target specific compounds with advantages over antibodies.

The two-step immobilization method described herein is especially useful for the immobilization of a SAM and amine-terminated aptamer onto a gold SPR sensing surface. The presently described SPR sensor provides advantages, such as low sample consumption, the lack of labeling requirement, high sensitivity, and fast response time. Additional advantages of the two-step immobilization method include demonstrable cost efficiency, good reversibility uniform density, and use as a robust and specific blood protein detection platform.

Example 3

Kits

The sensor described herein can be provided in the form of kits of parts. For example the amine-terminated aptamers can be included as a molecule alone or already attached to a substrate. Additional components can also be included and comprise microfluidic chip, reference standards, and additional components identifiable by a skilled person upon reading of the present disclosure. Also, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (such as wash buffers and the like).

It is to be understood that kits for various detection applications can include diagnostic kits, biomarker discovery kits, environmental testing kits, biohazard detection kits and/or bioweapons detection kits. The kits are useful for detecting targets in life science and analytical chemistry applications and can be prepared based on the methods disclosed herein.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

sensor, and emitting a detection signal in the presence of a specific interaction between the target entity and the sensor.

2. The sensor of claim 1, wherein the aptamer includes a nucleotide sequence capable of interacting with a specific target entity.

3. The sensor of claim 2, wherein the aptamer comprises 5'-NH$_2$—(CH$_2$)$_6$-GGTTGGTGTGGTTGG-3' [SEQ ID NO: 1] or 5'-NH$_2$—(CH$_2$)$_6$-CTATCAGTCCGTGGTAGGGCA-GGTTGGGGTGACT-3' [SEQ ID NO: 2].

4. The sensor of claim 1, wherein the sensor is capable of interacting with one or more target entities selected from: a large biomolecule, a small biomolecule, an organic molecule, a small molecule, a nucleic acid, a metal ion, a protein, an enzyme, a peptide, a drug, a dye, a cancer cell, a virus, a hormone, or a microorganism.

5. The sensor of claim 4, wherein target entity sample is selected from the group consisting of a biological sample, an environmental sample, a chemical sample, a pharmaceutical sample, a food sample, an agricultural sample, and a veterinary sample.

6. The sensor of claim 4, wherein the protein is a blood protein.

7. The sensor of claim 1, where the SAM layer comprises 3-mercaptopropionic acid (MPA).

---

---

What is claimed is:

1. A sensor for detecting the presence of a target entity, the sensor comprising:
   a self-assembly monolayer (SAM) layer attached to a substrate, the SAM layer being a mixed length spacer layer;
   an amine moiety immobilized on the SAM layer; and
   an aptamer immobilized on the amine moiety;
   the sensor being capable of being excited by an energy source, emitting a baseline signal in the absence of any specific interaction between the target entity and the 8. The sensor of claim 1, wherein the amine moiety comprises N-hydroxysuccinimide (NHS).

9. The sensor of claim 1, wherein the amine moiety comprises N-(3-dimethylaminopropyl)-N-ethylcarbodiimide hydrochloride (EDC).

10. The sensor of claim 1, wherein the aptamer is a single-stranded nucleic acid or a double-stranded nucleic acid.

11. The sensor of claim 1, wherein the aptamer comprises DNA, RNA, or both DNA and RNA.

12. The sensor of claim 1, wherein the sensor has a tunable detectable range capable of pM to nM detection.

13. A method of determining a presence of a target entity in a sample comprising:
   i) contacting the sample with a sensor of claim 1;
   ii) exciting the sensor with an energy source; and,
   iii) determining the strength of a signal emitted by the sensor, thereby determining whether the target entity is present in the sample.

14. The method of claim 13, wherein the energy source is measured using surface plasmon resonance (SPR).

15. The method of claim 13, wherein the signal is detected in a response time of less than about one minute.

16. The method of claim 13, wherein the signal is detected in a response time of less than about one minute at about room temperature.

17. A kit for the detection of a target entity, comprising: a sensor of claim 1; and at least one container containing the sensor, where a sample may be added to the container.

18. A method for making a sensor of claim 1, comprising: i) immobilizing a self-assembled monolayer (SAM) layer to a substrate, wherein the SAM layer is a mixed-length spacer layer; and ii) immobilizing an amine-terminated aptamer to the SAM layer of step i).

19. The sensor of claim 1, wherein the SAM layer defines a plurality of SAM sites, and one or more of the plurality of SAM sites is non-occupied by the aptamer immobilized on the amine moiety, wherein the sensor further comprises a blocking agent on the non-occupied SAM sites.

20. The sensor of claim 19, wherein the blocking agent comprises ethanolamine.

\* \* \* \* \*